(12) United States Patent
Wang et al.

(10) Patent No.: US 10,722,201 B2
(45) Date of Patent: Jul. 28, 2020

(54) COMBINATION OF AN X-RAY TUBE AND A SOURCE GRATING WITH ELECTRON BEAM MANIPULATION

(71) Applicant: Rensselaer Polytechnic Institute, Troy, NY (US)

(72) Inventors: Ge Wang, Loudonville, NY (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 216 days.

(21) Appl. No.: 15/741,047

(22) PCT Filed: Jul. 27, 2016

(86) PCT No.: PCT/US2016/044287
§ 371 (c)(1),
(2) Date: Dec. 29, 2017

(87) PCT Pub. No.: WO2017/019782
PCT Pub. Date: Feb. 2, 2017

(65) Prior Publication Data
US 2018/0192981 A1    Jul. 12, 2018

Related U.S. Application Data

(60) Provisional application No. 62/197,301, filed on Jul. 27, 2015.

(51) Int. Cl.
*A61B 6/00* (2006.01)
*H01J 35/14* (2006.01)
(Continued)

(52) U.S. Cl.
CPC ............ *A61B 6/484* (2013.01); *A61B 6/032* (2013.01); *A61B 6/405* (2013.01); *A61B 6/4007* (2013.01);
(Continued)

(58) Field of Classification Search
CPC ..... A61B 6/484; A61B 6/4241; A61B 6/4291; A61B 6/4021; A61B 6/4035;
(Continued)

(56) References Cited

U.S. PATENT DOCUMENTS 9,600,910 B2    3/2017  Wang et al.
9,730,657 B2    8/2017  Wang et al.
(Continued)

FOREIGN PATENT DOCUMENTS

WO    2010150136 A1    12/2010
WO    2014125389 A1    8/2014
(Continued)

OTHER PUBLICATIONS

Miao et al., Motionless phase stepping in X-ray phase contrast imaging with a compact source, Nov. 26, 2013, PNAS, vol. 110, pp. 19268-19272. (Year: 2013).*
(Continued)

*Primary Examiner* — Christine S. Kim
(74) *Attorney, Agent, or Firm* — Murtha Cullina LLP; Anthony P. Gangemi

(57) ABSTRACT

Novel and advantageous systems and methods for performing X-ray imaging by using an X-ray source with source grating functionality incorporated therein are provided. An electron beam can be electromagnetically manipulated such that the X-ray source emits radiation in a pattern that is the same as if the radiation had already passed through a source grating.

20 Claims, 4 Drawing Sheets

(51) Int. Cl.
*A61B 6/03* (2006.01)
*H01J 29/48* (2006.01)

(52) U.S. Cl.
CPC .......... *A61B 6/4021* (2013.01); *A61B 6/4028* (2013.01); *A61B 6/4035* (2013.01); *A61B 6/4064* (2013.01); *A61B 6/4241* (2013.01); *A61B 6/4291* (2013.01); *H01J 35/14* (2013.01); *A61B 6/4225* (2013.01); *A61B 6/4233* (2013.01); *G21K 2207/005* (2013.01); *H01J 29/488* (2013.01)

(58) Field of Classification Search
CPC ..... A61B 6/4225; A61B 6/4233; A61B 6/032; A61B 6/4007; A61B 6/4028; A61B 6/405; A61B 6/4064; H01J 29/488; H01J 35/14; G21K 2207/005
See application file for complete search history.

(56) References Cited

U.S. PATENT DOCUMENTS

| | | | |
|---|---|---|---|
| 2005/0080466 A1 | 4/2005 | Homer | |
| 2009/0238334 A1* | 9/2009 | Brahme | A61B 6/022 378/41 |
| 2010/0080341 A1 | 4/2010 | Popescu et al. | |
| 2013/0108015 A1* | 5/2013 | Kottler | A61B 6/484 378/36 |
| 2015/0071402 A1 | 3/2015 | Handa | |
| 2015/0157286 A1 | 6/2015 | Wang et al. | |
| 2016/0113602 A1 | 4/2016 | Wang et al. | |
| 2016/0135769 A1 | 5/2016 | Wang et al. | |
| 2016/0166852 A1 | 6/2016 | Wang et al. | |
| 2017/0043041 A1 | 2/2017 | Wang et al. | |
| 2017/0360385 A1 | 12/2017 | Wang et al. | |
| 2017/0362585 A1 | 12/2017 | Wang et al. | |

FOREIGN PATENT DOCUMENTS

| | | |
|---|---|---|
| WO | 2015164405 A1 | 10/2015 |
| WO | 2016106348 A1 | 6/2016 |
| WO | 2016118960 A1 | 7/2016 |
| WO | 2016154136 A1 | 9/2016 |
| WO | 2016197127 A1 | 12/2016 |
| WO | 2017015381 A1 | 1/2017 |
| WO | 2017019782 A1 | 2/2017 |
| WO | 2017048856 A1 | 3/2017 |
| WO | 2017083849 A1 | 5/2017 |
| WO | 2017143247 A1 | 8/2017 |
| WO | 2017176976 A1 | 10/2017 |
| WO | 2017205379 A2 | 11/2017 |

OTHER PUBLICATIONS

Source Block Data Sheet [online] Source Ray, Inc., [Retrieved on Sep. 26, 2019]. Retrieved from Internet http://www.sourceray.com/sites/default/files/Low%20Power%20SourceBlocks%20Brochure.pdf (Year: 2019).*

Source Block Specification [online] Source Ray, Inc. [Retrieved on Sep. 26, 2019]. Retrieved from Internet https://sourceray.com/sites/default/files/Outline_SB-80-1K.pdf (Year: 2019).*

International Search Report/Written Opinion, PCT International Application No. PCT/US2016/044287, PCT/ISA/220, PCT/ISA/210, PCT/ISA/237, dated Nov. 2, 2016.

* cited by examiner

COMBINATION OF AN X-RAY TUBE AND A SOURCE GRATING WITH ELECTRON BEAM MANIPULATION

CROSS-REFERENCE TO RELATED APPLICATION

This application is a national stage application of International Patent Application No. PCT/US2016/044287, filed Jul. 27, 2016 which claims the benefit of U.S. Provisional Application Ser. No. 62/197,301, filed Jul. 27, 2015, both of which are incorporated herein by reference in their entireties, including any figures, tables, and drawings.

BACKGROUND

X-ray imaging is a powerful tool in many fundamental and practical applications. As a primary example, X-ray computed tomography (CT) is a cornerstone of modern hospitals and clinics. The dominating theory of X-ray imaging is generally based on the attenuation contrast mechanism.

X-ray gratings have been used for hybrid CT imaging in terms of attenuation, refraction, and small-angle scattering. This grating-based approach represents a paradigm shift in X-ray CT from gray-scale (attenuation) to true-color (attenuation, refraction, and small-angle scattering, which is also referred to as dark-field, and spectral) imaging.

In conventional X-ray imaging, the image contrast arises from varying linear attenuation coefficients. Attenuation-contrast-based imaging exhibits good performance only when strong attenuators are embedded in a weakly absorbing matrix, such as in the cases of bone-tissue and tissue-air interfaces. However, biological soft tissues include mainly light elements (e.g., hydrogen, carbon, nitrogen, and oxygen), and their compositions are quite homogeneous with little density variation. The attenuation-contrast between soft tissue features is often insufficient to reflect pathological changes.

In particular, many healthy tissues display similar characteristics in current X-ray images as those of diseased tissues, such as tumors. For example, fibro-glandular tissue can have a density of 1.035 $cm^{-3}$ and an attenuation coefficient of 0.80 $cm^{-1}$, and cancerous tissue can have a density of 1.045 $cm^{-3}$ and an attenuation coefficient of 0.85 $cm^{-1}$. Given inherent measurement noise, it is challenging to discern such cancerous tissue from the healthy tissue, as well as other soft tissue features such as those reflecting musculoskeletal healing. Therefore, attenuation-contrast-based imaging is unable to differentiate early-stage tumors and soft tissues.

Use of X-ray gratings can provide for not only attenuation but also phase-contrast and dark-field information. An X-ray grating-based imaging approach typically includes an ordinary X-ray source, and a source grating (often known as G0), and a phase grating (often known as G1) and an analyzer grating (often known as G2) are also typically used. The main purpose of the source grating is to provide sufficient spatial coherence for differential phase-contrast imaging. The source grating can have a micrometer-range period, such as a period of 50 µm or about 50 µm. It is difficult, however, to make a high-quality and large area source grating.

BRIEF SUMMARY

Embodiments of the subject invention provide novel and advantageous systems and methods for performing X-ray imaging by using an X-ray source with source grating functionality incorporated therein (e.g., via electromagnetic manipulation of the electron beam(s) within the X-ray source). The X-ray source can be, for example, an X-ray tube, though embodiments are not limited thereto. The systems and methods of embodiments of the subject invention present new opportunities in phase-contrast X-ray imaging (or X-ray grating-based imaging), shorten X-ray grating-based imaging time, increase configuration flexibility, increase efficiency of heat management, increase cost-effectiveness, and have many applications, including biomedical applications.

In an embodiment, an imaging system can comprise an X-ray radiation source having source grating functionality incorporated therein, such that the X-ray source is configured to emit X-ray radiation in a pattern that is indistinguishable from that of X-ray radiation that would have passed through a source grating whose functionality has been incorporated into the X-ray source. The system can further comprise a detector, a phase grating positioned between the X-ray source and the detector, and an analyzer grating positioned between the phase grating and the detector, and the system can specifically exclude a source grating.

In another embodiment, a system as described herein can be used to perform a method of imaging, the method comprising: providing X-ray radiation to a sample to be imaged using the X-ray radiation source; collecting the X-ray radiation with a detector; and analyzing data from the detector to obtain an image. X-ray diffraction fringes, phase-shift information, and dark-field information can be extracted from the data from the detector.

DETAILED DESCRIPTION

Embodiments of the subject invention provide novel and advantageous systems and methods for performing X-ray imaging by using an X-ray source with source grating functionality incorporated therein (e.g., via electromagnetic manipulation of the electron beam(s) within the X-ray source). The X-ray source can be, for example, an X-ray tube, though embodiments are not limited thereto. The systems and methods of embodiments of the subject invention present new opportunities in phase-contrast X-ray imaging (or X-ray grating-based imaging), shorten X-ray grating-based imaging time, increase configuration flexibility, increase efficiency of heat management, increase cost-effectiveness, and have many applications, including biomedical applications.

Figure 1:
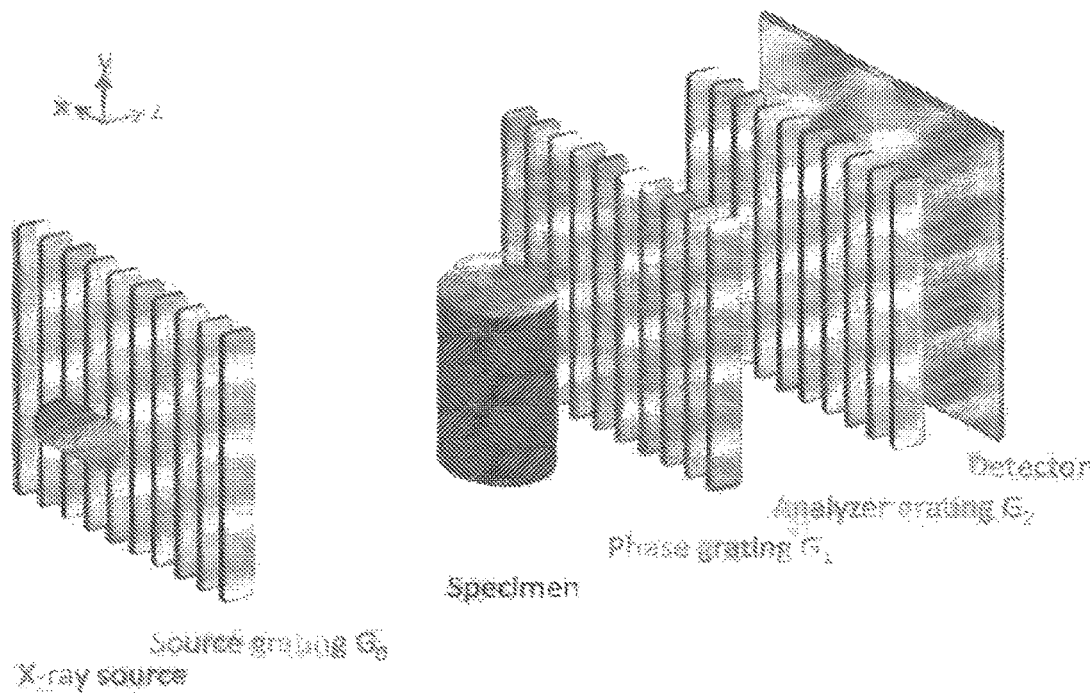
FIG. 1 shows a grating-based X-ray interferometer that can be used in X-ray grating-based imaging.

FIG. 1 shows a grating-based X-ray interferometer that can be used in X-ray grating-based imaging (phase-contrast X-ray imaging). FIG. 1 is from Burger et al. (Optics Express 22, 32107-32118 2014; which is hereby incorporated herein by reference in its entirety). Referring to FIG. 1, the interferometer can include an X-ray source and a source grating G0. The system can also include a phase grating G1, an analyzer grating G2, and a detector. The sample being imaged can be placed between the source grating G0 and the phase grating G1. Phase-shift and dark-field information can be extracted, for example using phase stepping, where the analyzer grating G2 or phase grating G1 is scanned over one G2 grating period. The subject application shares some concepts with International Patent Application No. PCT/US2016/043154 (Wang et al.), which is hereby incorporated by reference herein in its entirety.

Figure 2:
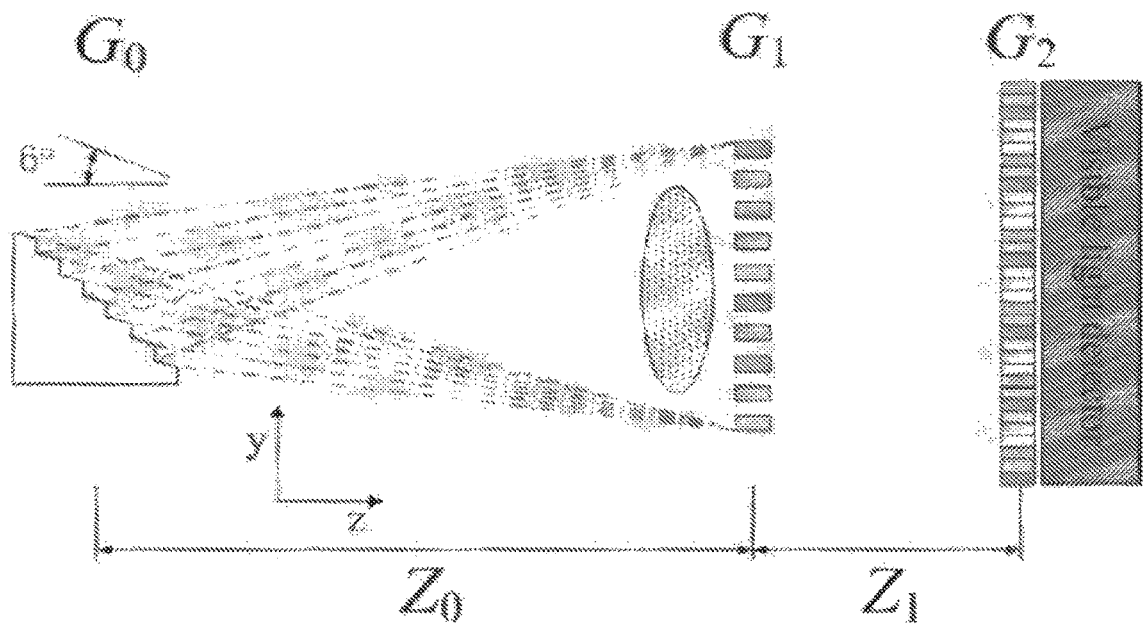
FIG. 2 shows a cross-sectional view of components of an X-ray imaging system for demonstrating principles of non-absorption grating X-ray phase-contrast imaging.

FIG. 2 shows a cross-sectional view of components of an X-ray imaging system and demonstrates principles of non-absorption phase-contrast X-ray grating-based imaging. The system can include a source grating G0 (e.g., a ladder-shaped multi-line source grating), a phase grating G1, an analyzer grating G2, and a detector, which can be a structured scintillator. FIG. 2 is from Du et al. (Optics Express, 22669, November 2011; which is hereby incorporated herein by reference in its entirety).

Referring again to FIG. 1, to improve the efficiency of the system, the source grating G0 can be combined with the X-ray source (e.g., an X-ray tube). An X-ray source typically includes a metallic target (anode or anode target), and the source grating (G0) configuration could be implemented in the metallic target inside the X-ray source. However, embodiments of the subject invention can combine the functionality of the source grating G0 with the X-ray source by electromagnetically manipulating the electron beam(s) within the X-ray source (e.g., instead of implementing the source grating (G0) configuration in the metallic target). That is, the X-ray source can achieve a G0 grating effect with the normal metallic target within the X-ray source through the use of electron beam manipulation.

A key idea related to embodiments of the subject invention is that an electron beam can be easily controlled, for example with coils. Thus, a controlled electron beam can implement the G0 effect within the X-ray source in a flexible and cost-effective manner that does not require complex components. The electron beam(s) can be controlled based on electromagnetic theory and techniques that are known and understood in a general sense. In addition, micro-fabrication technologies and/or nano-fabrication technologies can be used with embodiments of the subject invention. For example, graphene and/or nanotubes can be used with an X-ray source (e.g., for fine-tuning the electro-magnetic field such that the electron beam(s) are transmitted in a desirable configuration towards the metallic target in the source).

In many embodiments, a scanning mechanism can be implemented in the X-ray source (e.g., an X-ray tube). One or more electron beams can be electromagnetically manipulated or steered within the X-ray source to implement or trace a G0 grating pattern (i.e., to implement the functionality of the source grating within the X-ray source). The X-ray source can be configured such that the electron beam manipulation can occur before the electron beam(s) reach the metallic target within the X-ray source. In this way, the X-rays exiting the X-ray source can in the same state as those that have passed through the source grating in a conventional system that includes an X-ray source and a separate source grating. In an embodiment, an electron beam can be manipulated or steered within the X-ray source to implement or trace a G0 grating pattern such that the beam is split into a plurality of beamlets and nominal beamlets are wider than gaps between the beamlets.

Embodiments of the subject invention include X-ray sources that can emulate many different types of source gratings, including one-dimensional (1D) gratings, two-dimensional (2D) gratings, and three-dimensional (3D) gratings. In addition, X-ray sources of embodiments of the subject invention can the shape of an electron beam within the X-ray source. For example, a circular electron beam (i.e., a cross-section of the beam taken through a plane perpendicular to the direction of propagation of the beam is circular) can be electromagnetically manipulated and converted into a different shape beam, such as a planar beam or a flat beam (i.e., a cross-section of the beam taken through a plane perpendicular to the direction of propagation of the beam has a shape of a line and a cross-section of the beam taken through a plane parallel to the direction of propagation of the beam has a shape of a plane or rectangle).

Figure 4:
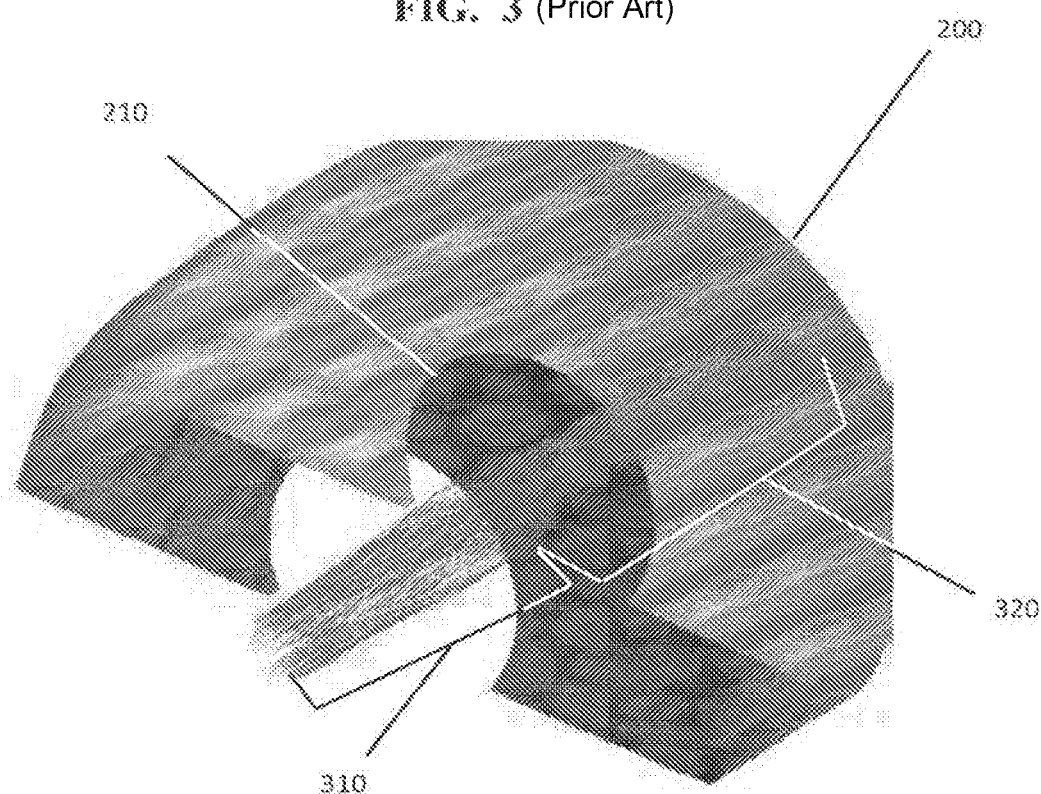
FIG. 4 shows a cutaway view of a portion of a focusing element that can be used in an X-ray source according to an embodiment of the subject invention.
Figure 5A:
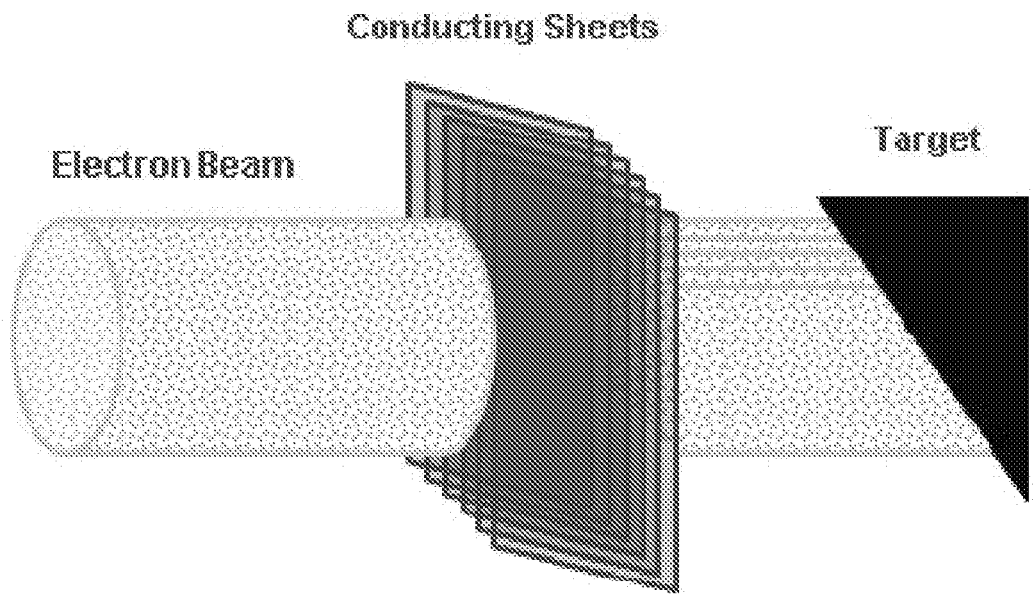
FIG. 5A shows a perspective view of a scheme for manipulating an electron beam within an X-ray source according to an embodiment of the subject invention.
Figure 5B:
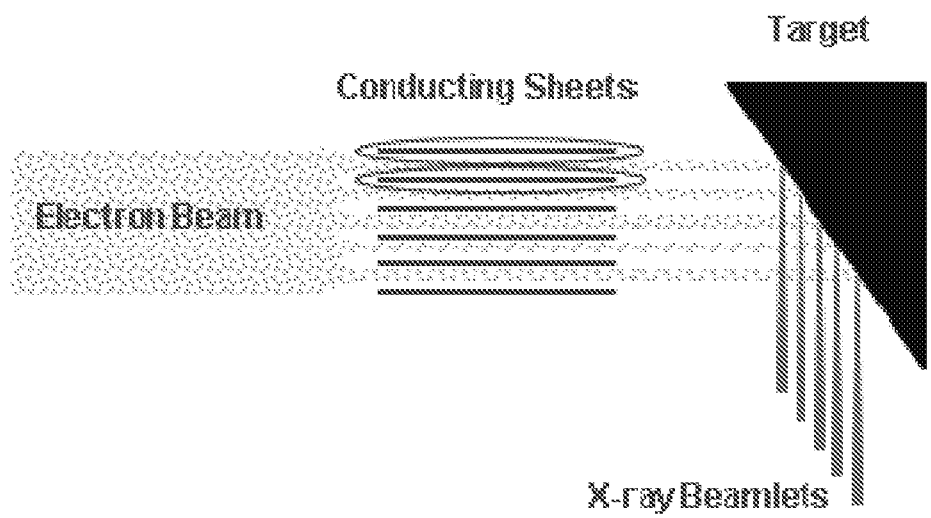
FIG. 5B shows a top view of the scheme shown in FIG. 5A.

FIG. 4 shows a cutaway view of a portion of a focusing element that can be used in an X-ray source according to an embodiment of the subject invention. Referring to FIG. 4, the focusing element 200 can be shaped such that the incoming electron beam 310 (depicted as including a plurality of individual electron orbits) can be focused into a different shape or configuration in the outgoing electron beam 320. As depicted in FIG. 4, the focusing element 200 can be a solenoid having an aperture 210 (e.g., an elliptical aperture) through which the electron beam passes, and the incoming electron beam 310 can be circular and can be transformed into a flat or planar outgoing electron beam 320. These depictions are for exemplary purposes, and embodiments are not limited thereto. It should also be noted that FIG. 4 is a cutaway showing only a portion of a focusing element 200; in this case the pole-piece of the solenoid is depicted.

According to embodiments of the subject invention, an electron beam can be focused into many different shapes, including but not limited to a focal point or a planar sheet. The electron beam can be electromagnetically steered to the metallic target. For example, the beam can be split into a plurality of beamlets such that beamlets are wider than gaps between the beamlets. As another example, the beam can be split into a plurality of beamlets such that beamlets are narrower than gaps between the beamlets. In either of these examples, the widths of the beamlets and the widths of the gaps between the beamlets can each be uniform, non-uniform, or a mixture thereof.

In the case of implementing the functionality of a 1D source grating into the X-ray source, a scanning electron sheet results in much higher X-ray flux than a scanning electron focal spot. That is, if the beam is focused into a sheet shape, the X-ray flux can be higher than if it is focused into a spot shape. In certain instances, focusing into a sheet shape may be easier to accomplish than focusing into a spot.

In an embodiment, an electron beam can be focused into a set of electron sheets (e.g., a set of parallel electron sheets). The original beam can have a large aperture and can go through an electromagnetic grating within the X-ray source to be split into multiple electron sheets (or tall, very narrow beams).

Because electrons are negatively charged, when manipulating an electron beam in an X-ray source according to embodiments of the subject invention, the original electrons of the beam must be steered through a negatively-charged pattern (e.g., a periodic pattern) to be deflected into the desired configuration. For example, a set of parallel sheets or rods can be negatively charged so that incoming electrons will be repelled from these negatively-charged barriers and pass between them, forming the desired configuration of the electron flow. The structures used to steer the electron beam(s) (e.g., sheets, rods, coils) can be made of any suitable material. In certain embodiments, the structures used to steer the electron beam(s) (e.g., sheets, rods, coils) can be made of graphene or carbon nanotubes. For example, sheets can be made of graphene, and rods can be made of nanotubes, though embodiments are not limited thereto.

Figure 3:
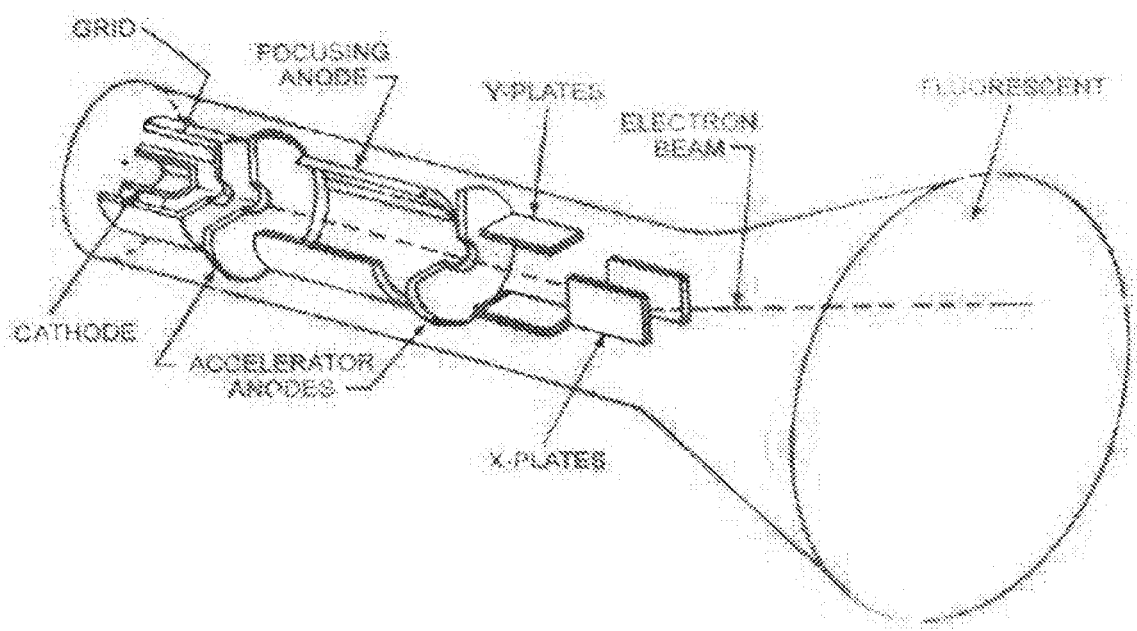
FIG. 3 shows a cross-sectional view of a cathode ray tube.

FIG. 3 shows a cross-sectional view of a cathode ray tube and is from Circuits Today (http://www.circuitstoday.com/crt-cathode-ray-tube; which is hereby incorporated herein by reference in its entirety). The cathode ray tube can include an electron gun for producing a stream of electrons, focusing and accelerating anodes for producing a narrow and sharply focused electron beam, horizontal and vertical deflection plates for controlling the beam path, and an evacuated glass envelope with a phosphorescent screen that produces visible light when struck by a high velocity electron beam.

In an embodiment of the subject invention, the concept of a cathode ray tube can be enhanced and used in an X-ray tube as an X-ray source. The source grating (G0) of an X-ray imaging system can be integrated into the X-ray tube so that the X-ray tube directly emits spatially-coherent X-ray beams as if they are already through the source grating (G0).

In an X-ray source as described herein, the anode target can have any suitable shape. For example, the anode target can be shaped as at least one spot, at least one line, or an extended area. In a particular embodiment, the anode target can have the same area as the source grating (G0) that would otherwise be present in the imaging system (i.e., the source grating whose functionality is being implemented in the X-ray source). As an example, the source grating (G0) in an X-ray imaging system typically has an area of about 50-500 mm$^2$ (e.g., 15 mm by 15 mm=225 mm$^2$), and the period of the source grating (G0) is typically in a range of from 15 μm to 80 μm. An anode target can therefore have an area in a range of from 50 mm$^2$ to 500 mm$^2$ (e.g., 15 mm by 15 mm=225 mm$^2$), and the X-ray source can be configured to produce X-rays as if they had already gone through a source grating (G0) having a period in a range of from 15 μm to 80 μm.

Figure 6:
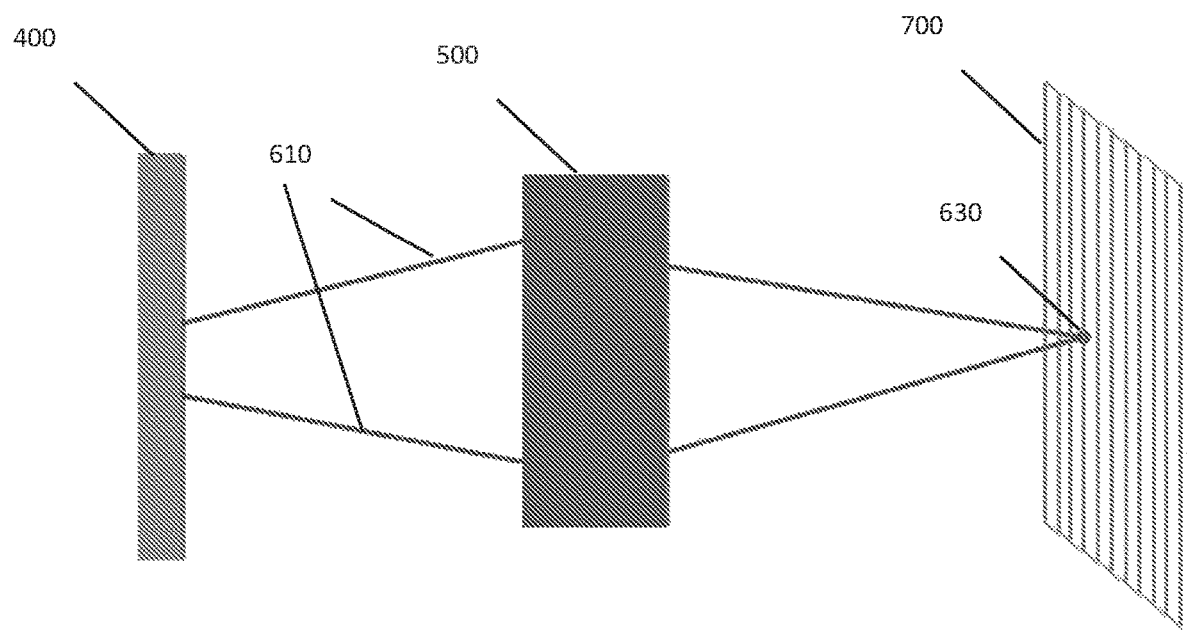
FIG. 6 shows a view of beam focusing within an X-ray source according to an embodiment of the subject invention.

An electron beam can be focused within the X-ray source to any suitable pattern. For example, an electron beam can be focused into a focal spot with a small radius (e.g., a radius of 5 μm, or less than 6 μm). The accelerated electron beam can hit the anode target in a progressive scan mode that traces the transmission pattern of the source grating (G0) whose functionality is being incorporated into the X-ray source, creating a sufficiently coherent virtual line source. This concept is shown in FIG. 6, in which an electron beam 610 can be focused into a focal spot 630 to generate coherent X-rays. The focal spot 630 can be electromagnetically scanned to trace the transmission pattern of the G0 grating whose functionality is being incorporated into the X-ray source. In FIG. 6, reference numeral 400 is the cathode, reference numeral 500 is the focusing element (e.g., focusing plate), and reference numeral 700 is the anode target.

The limiting factor for single exposure in a scheme as depicted in FIG. 6 can be the heat capacity of the focal spot. In an embodiment of the subject invention, the exposure time can be short at each focal spot. For example, the exposure time at each focal spot can be less than 10 milliseconds (ms), less than 5, ms, less than 2 ms, less than 1 ms, about 1 ms, or 1 ms. If the exposure time at each focal spot is 1 ms, it can take 1 second to scan a grid line of the G0 grating (that would otherwise be present) (e.g., if it takes 1000 focal spots to make up a grid line). At this scanning speed, if there are 10 grid lines, it can take 10 seconds to scan over the entire grating that would otherwise be present. The heat storage capacity of an anode target can be, for example, about 115,000 heat units (HU). For a 100 kVp, 5 mA X-ray tube, the heat generated by the electric beam hitting the anode target can be calculated from HU=100 kV×5 mA×0.001 seconds=0.5 HU. This is significantly lower than the heat storage capacity of the anode target (115,000 HU), so a static anode can be a valid option, which significantly reduces the design and fabrication cost of the X-ray source.

Embodiments of the subject invention provide systems and methods for performing imaging by using a radiation source with source grating functionality incorporated therein (e.g., via electromagnetic manipulation of the electron beam(s) within the radiation source). The systems and methods of embodiments of the subject invention present new opportunities in phase-contrast X-ray imaging, shorten phase-contrast X-ray imaging time, increase configuration flexibility, increase efficiency of heat management, increase cost-effectiveness, and have many applications, including biomedical applications.

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1. An imaging system, comprising:
a radiation source (e.g., an X-ray source) having source grating functionality incorporated therein, such that the radiation source is configured to (electromagnetically manipulate an electron beam therein such that the X-ray source) emit(s) radiation (e.g., spatially-coherent X-ray beams or beamlets) in a pattern that is indistinguishable from that of radiation (e.g., X-ray beams or beamlets) that would have passed through a source grating whose functionality has been incorporated into the radiation source.

Embodiment 2. The system according to embodiment 1, further comprising a detector for detecting radiation (e.g., X-rays) from the radiation source.

Embodiment 3. The system according to embodiment 2, further comprising a phase grating positioned between the radiation source and the detector.

Embodiment 4. The system according to embodiment 3, further comprising an analyzer grating positioned between the phase grating and the detector.

Embodiment 5. The system according to embodiment 2, further comprising an analyzer grating positioned between the radiation source and the detector.

Embodiment 6. The system according to any of embodiments 3-4, configured such that a subject to be imaged is positioned between the radiation source and the phase grating or between the phase grating and the detector.

Embodiment 7. The system according to any of embodiments 1-6, wherein the system excludes a source grating.

Embodiment 8. The system according to any of embodiments 1-7, wherein the radiation source is configured to manipulate an electron beam within the radiation source to trace a pattern of the source grating whose functionality has been incorporated into the radiation source.

Embodiment 9. The system according to embodiment 8, wherein the radiation source is configured to manipulate the electron beam within the radiation source before the electron beam reaches a metallic (anode) target of the radiation source.

Embodiment 10. The system according to any of embodiments 1-7, wherein the radiation source comprises a metallic (anode) target that is in a motion mode (e.g., rotation mode).

Embodiment 11. The system according to any of embodiments 1-10, wherein the radiation source comprises at least one negatively-charged structure configured to steer the electron beam into a desirable (e.g., predetermined) pattern within the radiation source.

Embodiment 12. The system according to embodiment 11, wherein the at least one negatively-charged structure configured to steer the electron beam within the radiation source comprises a plate configured to split an electron beam (e.g., into a one-dimensional (1D) array of beamlets or a two-dimensional (2D) array of beamlets).

Embodiment 13. The system according to any of embodiments 11-12, wherein the at least one negatively-charged structure configured to steer the electron beam within the radiation source comprises a rod.

Embodiment 14. The system according to any of embodiments 11-13, wherein the at least one negatively-charged structure configured to steer the electron beam within the radiation source comprises a coil.

Embodiment 15. The system according to any of embodiments 11-14, wherein the radiation source comprises a plurality of negatively-charged structures configured to steer the electron beam within the radiation source.

Embodiment 16. The system according to embodiment 15, wherein the plurality of negatively-charged structures configured to steer the electron beam within the radiation source comprises a set of parallel plates configured to split an electron beam into a plurality of electron sheets.

Embodiment 17. The system according to any of embodiments 15-16, wherein the plurality of negatively-charged structures configured to steer the electron beam within the radiation source comprises a set of rods (which can be parallel to each other) configured to split an electron beam.

Embodiment 18. The system according to any of embodiments 15-17, wherein the plurality of negatively-charged structures configured to steer the electron beam within the radiation source comprises a set of coils.

Embodiment 19. The system according to any of embodiments 11-18, wherein the at least one negatively-charged structure configured to steer the electron beam within the radiation source comprises a negatively-charged structure comprising graphene.

Embodiment 20. The system according to any of embodiments 11-19, wherein the at least one negatively-charged structure configured to steer the electron beam within the radiation source comprises a negatively-charged structure comprising carbon nanotubes.

Embodiment 21. The system according to any of embodiments 11-20, wherein the at least one negatively-charged structure configured to steer the electron beam within the radiation source comprises a negatively-charged structure comprising a metal material.

Embodiment 22. The system according to any of embodiments 11-18, wherein each negatively-charged structure (configured to steer the electron beam within the radiation source) present comprises graphene.

Embodiment 23. The system according to any of embodiments 11-18, wherein each negatively-charged structure (configured to steer the electron beam within the radiation source) present comprises carbon nanotubes.

Embodiment 24. The system according to any of embodiments 11-18, wherein each negatively-charged structure (configured to steer the electron beam within the radiation source) present comprises a metal material.

Embodiment 25. The system according to any of embodiments 11-21, wherein each plate present in the at least one negatively-charged structure (configured to steer the electron beam within the radiation source) comprises graphene.

Embodiment 26. The system according to any of embodiments 11-21, wherein each rod present in the at least one negatively-charged structure (configured to steer the electron beam within the radiation source) comprises carbon nanotubes.

Embodiment 27. The system according to any of embodiments 11-21, wherein each coil present in the at least one negatively-charged structure (configured to steer the electron beam within the radiation source) comprises a metal material.

Embodiment 28. The system according to any of embodiments 1-27, wherein the radiation source comprises a metallic (anode) target, and wherein the target has a shape of at least one spot, at least one line, or an extended area.

Embodiment 29. The system according to embodiment 28, wherein the target has a shape of at least one spot.

Embodiment 30. The system according to embodiment 28, wherein the target has a shape of at least one line.

Embodiment 31. The system according to embodiment 28, wherein the target has a shape of an extended area.

Embodiment 32. The system according to embodiment 31, wherein the target has an area that is equal to that of the source grating whose functionality has been incorporated into the radiation source.

Embodiment 33. The system according to any of embodiments 31-32, wherein the target has an area in a range of from 50 mm$^2$ to 500 mm$^2$.

Embodiment 34. The system according to any of embodiments 31-33, wherein the target has an area of 225 mm$^2$ (or about 225 mm$^2$).

Embodiment 35. The system according to any of embodiments 31-34, wherein the target is a 15 mm by 15 mm target.

Embodiment 36. The system according to any of embodiments 1-35, wherein the source grating whose functionality has been incorporated into the radiation source has a period in a range of from 15 μm to 80 μm.

Embodiment 37. The system according to any of embodiments 1-36, wherein the source grating whose functionality has been incorporated into the radiation source has a period of 50 μm (or about 50 μm).

Embodiment 38. The system according to any of embodiments 1-37, wherein the radiation source comprises a focusing element configured to focus an electron beam into a desired shape.

Embodiment 39. The system according to any of embodiments 1-37, wherein the radiation source comprises a focusing element configured to focus an electron beam into a desired shape on a (the) metallic target within the radiation source.

Embodiment 40. The system according to embodiment 39, wherein the desired shape is a focal spot with a radius of less than 20 μm.

Embodiment 41. The system according to embodiment 39, wherein the desired shape is a focal spot with a radius of less than 6 μm.

Embodiment 42. The system according to embodiment 39, wherein the desired shape is a focal spot with a radius of 5 μm (or about 5 μm).

Embodiment 43. The system according to embodiment 39, wherein the desired shape is a line, such that the electron beam is focused into a flat beam.

Embodiment 44. The system according to any of embodiments 38-39, wherein the desired shape is a(t least one) line, such that the electron beam is focused into a flat beam.

Embodiment 45. The system according to any of embodiments 37-44, wherein the focusing element is a focusing plate.

Embodiment 46. The system according to any of embodiments 37-44, wherein the focusing element comprises at least one focusing plate.

Embodiment 47. The system according to any of embodiments 37-44, wherein the focusing element comprises a plurality of focusing plates.

Embodiment 48. The system according to any of embodiments 37-44, wherein the focusing element comprises a solenoid with an aperture therethrough.

Embodiment 49. The system according to embodiment 48, wherein the aperture is elliptical.

Embodiment 50. The system according to any of embodiments 40-42, wherein the radiation source is configured such that an exposure time for each focal spot is less than 10 milliseconds (ms).

Embodiment 51. The system according to any of embodiments 40-42, wherein the radiation source is configured such that an exposure time for each focal spot is less than 5 ms.

Embodiment 52. The system according to any of embodiments 40-42, wherein the radiation source is configured such that an exposure time for each focal spot is less than 2 ms.

Embodiment 53. The system according to any of embodiments 40-42, wherein the radiation source is configured such that an exposure time for each focal spot is less than 1 ms.

Embodiment 54. The system according to any of embodiments 40-42, wherein the radiation source is configured such that an exposure time for each focal spot is 1 ms (or about 1 ms).

Embodiment 55. The system according to any of embodiments 1-54, wherein the radiation source comprises a metallic target that is a static anode or a rotating anode.

Embodiment 56. The system according to any of embodiments 1-55, wherein the radiation source is configured to split an electron beam into a plurality of beamlets such each beamlet is wider than each gap between the beamlets.

Embodiment 57. The system according to any of embodiments 1-55, wherein the radiation source is configured to split an electron beam into a plurality of beamlets such each beamlet is narrower than each gap between the beamlets.

Embodiment 58. The system according to any of embodiments 56-57, wherein the width of each beamlet is the same as that of every other beamlet.

Embodiment 59. The system according to any of embodiments 56-58, wherein a width of each gap between beamlets is the same as that of every other gap between beamlets.

Embodiment 60. The system according to any of embodiments 56-57, wherein the width of at least one beamlet is the same as that of at least one other beamlet.

Embodiment 61. The system according to any of embodiments 56-57 and 60, wherein a width of at least one gap between beamlets is the same as at least one other gap between beamlets.

Embodiment 62. The system according to any of embodiments 56-57, wherein the width of each beamlet is different from that of every other beamlet.

Embodiment 63. The system according to any of embodiments 56-57 and 62, wherein a width of each gap between beamlets is different from that of every other gap between beamlets.

Embodiment 64. The system according to any of embodiments 1-63, wherein the source grating whose functionality has been incorporated into the radiation source is a 1D source grating.

Embodiment 65 The system according to any of embodiments 1-63, wherein the source grating whose functionality has been incorporated into the radiation source is a 2D source grating.

Embodiment 66. A method of imaging using the system according to any of embodiments 1-65, the method comprising:

providing radiation (e.g., X-ray radiation) to a sample to be imaged using the radiation source;

collecting the radiation (e.g., X-ray radiation) with a (the) detector; and analyzing data from the detector to obtain an image.

Embodiment 67. The method according to embodiment 66, wherein analyzing data from the detector to obtain an image comprises extracting diffraction fringes (e.g., X-ray diffraction fringes), phase-shift information, and dark-field information from the data from the detector.

Embodiment 68. The system according to any of embodiments 1-65, further comprising a (non-transitory) machine readable medium (e.g., computer readable medium) having machine-executable (e.g., computer executable) instructions (stored thereon) for performing the step of analyzing data from the detector according to the method of any of embodiments 66-67, wherein the machine readable medium is in operable communication with the detector.

Embodiment 69. The system according to any of embodiments 1-65 and 68, or the method according to any of embodiments 66-67, wherein a (the) detector of the imaging system is a photon-counting detector, such that spectral information is included in data of the detector.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Du et al., "Non-absorption grating approach for X-ray phase contrast imaging," vol. 19, No. 23, Optics Express, 22669 (November 2011); http://www.ncbi.nlm.nih.gov/pubmed/22109147.

Burger et al., "Regularized iterative integration combined with non-linear diffusion filtering for phase-contrast x-ray computed tomography," Opt. Express 22, 32107-32118 (2014); http://www.opticsinfobase.org/oe/abstract.cfm?uri=oe-22-26-32107 http://www.circuitstoday.com/crt-cathode-ray-tube http://ieeexplore.ieee.org/stamp/stamp.jsp?arnumber=1420641 http://www.nanocyl.com/jp/CNT-Expertise-Centre/Carbon-Nanotubes

Shi et al., An edge-on charge-transfer design for energy-resolved x-ray detection, Physics in Medicine and Biology, Volume 61, Number 11, 2016

Wang et al., International Patent Application Publication No. WO2016/106348

Wang et al., U.S. Patent Application Publication No. 2015/0157286

Wang et al., U.S. Patent Application Publication No. 2015/0170361

Wang et al., U.S. Patent Application Publication No. 2015/0193927

Wang et al., International Patent Application Publication No. WO2015/164405

Wang et al., U.S. Patent Application Publication No. 2016/0113602

Wang et al., U.S. Patent Application Publication No. 2016/0135769

Wang et al., U.S. Patent Application Publication No. 2016/0166852

Wang et al., International Patent Application Publication No. WO2016/106348

Wang et al., International Patent Application No. PCT/US2016/014769

Wang et al., International Patent Application No. PCT/US2016/023460

Wang et al., International Patent Application No. PCT/US2016/036057

Wang et al., International Patent Application No. PCT/US2016/043154

What is claimed is:

1. An imaging system, comprising:
   an X-ray source having source grating functionality incorporated therein, such that the X-ray source is configured to electromagnetically manipulate an electron beam therein such that the X-ray source emits X-ray radiation in a pattern that would have passed through a source grating whose functionality has been incorporated into the X-ray source;
   wherein the X-ray source is configured to split an electron beam into a plurality of beamlets such that each beamlet is narrower than each gap between the beamlets.

2. The system according to claim 1, further comprising:
   a detector for detecting X-rays from the X-ray source;
   a phase grating positioned between the X-ray source and the detector; and
   an analyzer grating positioned between the phase grating and the detector.

3. The system according to claim 2, configured such that a subject to be imaged is positioned between the X-ray source and the phase grating or between the phase grating and the detector.

4. The system according to claim 1, wherein the system excludes a source grating.

5. The system according to claim 1, wherein the X-ray source is configured to manipulate the electron beam within the X-ray source to trace a pattern of the source grating whose functionality has been incorporated into the X-ray source,
   wherein the X-ray source is configured to manipulate the electron beam within the X-ray source before the electron beam reaches a metallic target of the X-ray source.

6. The system according to claim 1, wherein the X-ray source comprises a metallic target that is in rotation mode or another motion mode,
   wherein the radiation source comprises a plurality of negatively-charged structures configured to steer the electron beam within the X-ray source,
   wherein the plurality of negatively-charged structures configured to steer the electron beam within the X-ray source comprises at least one of the following: a set of parallel plates configured to split an electron beam into a plurality of electron sheets; a set of rods configured to split an electron beam; and a set of coils.

7. The system according to claim 6, wherein each negatively-charged structure configured to steer the electron beam within the X-ray source comprises graphene or a metal material.

8. The system according to claim 1, wherein the X-ray source comprises a metallic target, and wherein the target has a shape of at least one spot, at least one line, or an extended area,
   wherein the target has an area that is equal to that of the source grating, whose functionality has been incorporated into the radiation source, and
   wherein the target has an area in a range of from 50 mm$^2$ to 500 mm$^2$.

9. The system according to claim 1, wherein the source grating whose functionality has been incorporated into the X-ray source has a period in a range of 15 μm to 80 μm.

10. The system according to claim 1, wherein the X-ray source comprises a focusing element configured to focus an electron beam into a desired shape on a metallic target within the X-ray source,
    wherein the desired shape is a focal spot with a radius of less than 20 μm, and
    wherein the focusing element comprises at least one focusing plate or a solenoid with an elliptical aperture therethrough.

11. The system according to claim 10, wherein the X-ray source is configured such that an exposure time for each focal spot is less than 10 milliseconds (ms).

12. The system according to claim 1, wherein the X-ray source comprises a focusing element configured to focus the electron beam into a desired shape on a metallic target within the X-ray source,
  wherein the desired shape is at least one line, such that the electron beam is focused into a flat beam, and
  wherein the focusing element comprises at least one focusing plate or a solenoid with an elliptical aperture therethrough.

13. The system according to claim 1, wherein the X-ray source comprises a metallic target that is a static anode or a rotating anode.

14. The system according to claim 1, wherein the widths of the beamlets or the widths of the gaps between the beamlets are uniform.

15. The system according to claim 1, wherein the widths of the beamlets or the widths of the gaps between the beamlets are non-uniform.

16. The system according to claim 1, wherein a detector of the imaging system is a photon-counting detector, such that spectral information is included in data of the detector.

17. The system according to claim 1, wherein the source grating whose functionality has been incorporated into the radiation source is a 1D source grating or a 2D source grating.

18. A method of imaging using the system according to claim 1, the method comprising:
  providing the X-ray radiation to a sample to be imaged using the X-ray source;
  collecting the X-ray with a detector of the system; and
  analyzing data from the detector to obtain an image.

19. The method according to claim 18, wherein analyzing data from the detector to obtain an image comprises extracting X-ray diffraction fringes, phase-shift information, and dark-field information from the data from the detector.

20. The method according to claim 18, wherein a detector of the imaging system is a photon-counting detector, such that spectral information is included in data of the detector.

* * * * *